US005762608A

United States Patent [19]

Warne et al.

[11] Patent Number: 5,762,608
[45] Date of Patent: *Jun. 9, 1998

[54] SCANNING X-RAY IMAGING SYSTEM WITH ROTATING C-ARM

[75] Inventors: James R. Warne, Washington, Pa.; Alvin Karloff, Framingham; Edward J. Botz, Winchester, both of Mass.; Michael D. Dabrowski, North Grosvenordale, Conn.

[73] Assignee: Hologic, Inc., Waltham, Mass.

[*] Notice: The portion of the term of this patent subsequent to Jan. 22, 2008, has been disclaimed.

[21] Appl. No.: 337,995

[22] Filed: Nov. 10, 1994

Related U.S. Application Data

[60] Continuation of Ser. No. 980,531, Nov. 23, 1992, abandoned, which is a division of Ser. No. 360,347, Jun. 5, 1989, Pat. No. 5,165,410, which is a continuation-in-part of Ser. No. 204,513, Jun. 9, 1988, abandoned, which is a continuation-in-part of Ser. No. 50,726, May 15, 1987, abandoned.

[51] Int. Cl.⁶ .................................................. A61B 6/00
[52] U.S. Cl. ........................... 600/425; 378/55; 378/197
[58] Field of Search ................... 128/653.1; 378/54–55, 378/89, 119, 146, 193, 195–198; 600/425

[56] References Cited

U.S. PATENT DOCUMENTS

| Re. 34,511 | 1/1994 | O'Neill et al. ............... 128/653.1 |
|---|---|---|
| 3,803,417 | 4/1974 | Kok ............................ 250/447 |
| 3,944,830 | 3/1976 | Dissing ...................... 250/358 |
| 3,988,585 | 10/1976 | O'Neill et. al. ............ 250/363 |
| 4,012,636 | 3/1977 | Engdahl et al. ............ 250/363 |
| 4,107,532 | 8/1978 | MaCovski .................. 250/360 |
| 4,144,457 | 3/1979 | Albert ........................ 250/445 |
| 4,259,585 | 3/1981 | Novak ....................... 250/456 |
| 4,275,305 | 6/1981 | Racz et al. ................. 250/445 |
| 4,342,916 | 8/1982 | Jatteau et al. ............. 378/4 |
| 4,358,856 | 11/1982 | Steivender et al. ....... 378/167 |
| 4,365,343 | 12/1982 | Grady et al. .............. 378/181 |
| 4,495,645 | 1/1985 | Ohhashi ..................... 382/6 |
| 4,503,854 | 3/1985 | Jako . | |
| 4,515,165 | 5/1985 | Carrol ....................... 128/664 |
| 4,543,959 | 10/1985 | Sepponen .................. 128/653 |

(List continued on next page.)

FOREIGN PATENT DOCUMENTS

| 0 253 742 | 7/1987 | European Pat. Off. . |
|---|---|---|
| 0 265 302 | 9/1987 | European Pat. Off. . |
| 2238706 | 2/1974 | Germany . |
| 24 12 161.7 | 3/1974 | Germany . |
| 86/07531 | 12/1986 | WIPO . |
| 88/08688 | 11/1988 | WIPO . |
| 90/10859 | 9/1990 | WIPO . |

OTHER PUBLICATIONS

Rutt, B.K., et al., "High Speed, High-Precision Dual Photon Absorptiometry", Reprint of pester exhibited at meeting at the American Society of Bone and Mineral Research, Jun. 16, 1985, Washington, D.C.

Pearce, R.B., "DPA Gaining Strength in Bone Scanning Debate", *Diagnostic Imaging* (Jun. 1986).

Norland Corporation advertising brochure for OsteoStatus System pp. 1–8.

(List continued on next page.)

*Primary Examiner*—Ruth S. Smith
*Attorney, Agent, or Firm*—Hamilton, Brook, Smith & Reynolds, P.C.

[57] ABSTRACT

A multidiagnostic rectilinear scanner for conducting non-invasive diagnostic procedures of bodily tissue. Both transmission and emission studies are performed on a single scanner utilizing software modules for each kind of study. Dual energy x-ray and radioactive sources are used to perform radiographic and absorptiometry transmission measurements. A system and method of identifying regions of interest within tissue being scanned and recording the location of those regions provides an additional diagnostic capability.

25 Claims, 14 Drawing Sheets

U.S. PATENT DOCUMENTS

| | | | |
|---|---|---|---|
| 4,590,378 | 5/1986 | Platz | 250/363 |
| 4,618,133 | 10/1986 | Siczek | 269/323 |
| 4,649,560 | 3/1987 | Grady et al. | 378/196 |
| 4,651,732 | 3/1987 | Frederick | 128/303 |
| 4,653,083 | 3/1987 | Rossi | 378/196 |
| 4,657,755 | 4/1987 | Christensen et al. | 424/1.1 |
| 4,671,292 | 6/1987 | Matsuk | 128/660 |
| 4,716,581 | 12/1987 | Barud | 378/198 |
| 4,829,549 | 5/1989 | Vogel et al. | 378/55 |
| 4,856,044 | 8/1989 | Tanguy et al. | 378/55 |
| 4,887,286 | 12/1989 | Seidenberg | 378/170 |
| 4,907,252 | 3/1990 | Aichinger et al. | 378/99 |
| 4,922,915 | 5/1990 | Arnold et al. | 128/653 |
| 4,947,414 | 8/1990 | Stein | 378/55 |
| 5,042,486 | 8/1991 | Pfeiler et al. | 128/653 |
| 5,050,608 | 9/1991 | Watanabe et al. | 128/653 |
| 5,119,817 | 6/1992 | Allen | 128/653 |
| 5,165,410 | 11/1992 | Warne et al. | 128/653 |
| 5,261,404 | 11/1993 | Mick et al. | 128/653 |

OTHER PUBLICATIONS

A New Dimension in Dual–Photon Absorptiometry Novo Introduces the BMC–Lab 23, Light Years Ahead.

Lunar Radiation Corporation's Users Manual for Lunar DP3 Dual Photon Scanner.

Brochure, "Osteotek Bone Densitometry", Medical & Scientific Enterprises, Inc.

Sartoris, D.J. et al., "Trabecular Bone Density in the Proximal Femur: Quantitative CT Assessment", *Radiology*, 160:707–712 (1986).

Mazess, R.B., et al., "Spine and Femur Density Using Dual–Photon Absorptiometry in US White Women", *Bone and Mineral*, 2:211–219 (1987).

Weissberger, M.A., et al., "Computed Tomography Scanning for the Measurement of Bone Mineral in the Human Spine", *Journal of Computer Assisted Tomography*, 2:254–262 (Jul. 1978).

Saddler et al., "Multimodality Imaging of the Thyroid and Parathyroid Glands"; *J. Nuclear Medicine* 28(1):122–129 (Jan. 1987).

"Magna Scanner", Equipment Description, Sec. 1, pp. 4–6.

"Radioisotope Scanners, The Total Scanning system", Ohio Nuclear, Inc.

Raytheon Series 600 Nuclear Scanner Instruction Manual, pp. 1–6 and 1–11, (Feb. 25, 1972).

"Model 1735 PHO/DOT Medical Scanner Operation Manual", Nuclear Chicago, pp. 1–2 to 2–7.

Endo et al., "Patient Beam Positioning System Using CT Images", *Physics in Medicine & Biology*, 27 (1982).

Tremolieres, La Medicine Nucleaire, Electronique Applications, No. 20, pp. 71–83, (1981).

Kule et al., "Transmission Scanning: A Useful Adjunct to Conventional Emission Scanning for Accurately Keying Isotope Deposition to Radiographic Anatomy", *Dept. Radiology of the School of Medicine*, pp. 278,284 (Aug. 1966).

Genant, H., "Assesing Osteoporosis: CT's Quantitative Advantage", *Diagnostic Imaging*, (Aug. 1985).

Robb et al., "An Operator–interative, Computer–controlled System For High Fidelity Digitization And Analysis Of Biomedical Images" *Zie Voor Titel Boek, De 2e Pagina*, pp. 12–26.

*Bone Densitometry Market Research* (1986).

Wahner et al. "Assessment of Bone Mineral. Part 1" J. Nuclear Medicine, 25(10):1134–1141 (1984).

Mazess, "Dual photon Absorptiometry and Osteoporosis—Absorptiometric Instrumentation" Meting Publication.

Jacobsen, Final Progress Report, "Development of Dichromography Techniques", pp. 1–2 and 15–18 (May 31, 1968).

SCANNING X-RAY IMAGING SYSTEM WITH ROTATING C-ARM

RELATED U.S. APPLICATION

This application is a continuation of application Ser. No. 07/980,531 filed Nov. 23, 1992 now abandoned, which is a Divisional of Ser. No. 07/360,347 filed Jun. 5, 1989 (U.S. Pat. No. 5,165,410), which is a Continuation-in-Part of Ser. No. 07/204,513 filed Jun. 9, 1988 now abandoned, which is a Continuation-in-Part of Ser. No. 07/050,726 filed May 15, 1987 now abandoned.

BACKGROUND

The present invention relates to the fields of radiology and nuclear medicine, and in particular to the use of rectilinear scanners for the performing of a number of diagnostic studies of bodily tissue and organs.

The fields of radiology and nuclear medicine have long been concerned with the development of techniques for the non-invasive diagnosis of medical conditions of human or animal tissue. Generally procedures involve the use of x-ray radiation that is passed through a body to provide static or dynamic transmission studies, or alternatively, the use of radiopharmaceuticals that are introduced into the patient such that their distribution or concentration can be viewed by the detection of the resulting gamma ray emissions of variable intensity.

Initially these systems used an analog rectilinear scanner to generate static images wherein a scintillation-type gamma ray detector equipped with a focusing collimator was moved continuously, through a series of parallel sweeps, to scan the region under study.

Rectilinear scanners have more recently been used with a dual energy radioactive source for conducting transmission bone densitometry studies. Early analog devices have been used for conducting emission studies with an injected isotope as referenced above. In either case rectilinear scanners have seen very limited use due to the development of so-called "gamma camera" systems developed in the last decade.

Because of the interest in performing dynamic studies such as myocardial perfusion, wall motion, lung perfusion and lung ventilation, systems were developed to view the entire region of interest. These "gamma camera" systems utilized a large diameter sodium iodide crystal in conjunction with a matrix of photomultiplier tubes and a multichannel collimator to perform a large variety of emission studies. The problem with gamma cameras using scintillation detector crystals is that the resolution is limited by both the light coupler between the detector and the photomultiplier and, more importantly, by the scattering of the radiation emitted from the in vivo region of investigation. Even if the resolution of gamma cameras were adequate they do not produce an image of the tissue of actual size. Gamma camera systems are also extremely expensive, require a large space to be used, and necessitate a relatively high level of operator training. In addition, the use of gamma cameras for performing static studies has tended to lower their cost effectiveness due to there use on these low revenue static studies.

As a result of these factors, there is a need for a relatively inexpensive, portable and easy to use rectilinear scanner that can be used for diagnostic applications requiring the generation of static images. This will operate to free the gamma camera systems for performing the high revenue dynamic studies for which they are intended.

SUMMARY OF THE INVENTION

The present invention relates to the use of rectilinear scanners for performing emission and transmission studies to provide diagnostic non-invasive measurements of body tissue.

The apparatus utilizes a housing that can be easily adapted for the use of different radiation sources to conduct these diagnostic studies. For example, both a dual energy radioactive source, such as gadolinium-153, or an x-ray generator can be placed in the housing of the scanner assembly. The radioactive source can be used for conducting transmission studies, and the x-ray source can be used for conducting both transmission and fluorescence studies. The x-ray source, in analogy with the dual photon energy source commonly used in bone densitometry, can use two energy levels to provide an x-ray bone densitometer. Alternatively, the detector, collimator and software package can be replaced to permit the performing of emission scintigraphy studies. A number of interchangeable collimators are used having different focal lengths, and sensitivity and which are designed to operate for emitting isotopes with different energy levels. The wall thickness of the collimator columns is altered to compensate for differing energy levels.

As described in U.S. patent application Ser. No. 050,726 filed on May 15, 1987, a rectilinear scanner can be mounted on an assembly which permits the radiation source and detector to be rotated about a patient so that scanning can be conducted at any angle without having to move the patient. This permitted improved bone densitometry studies of patients suffering from bone degeneration. The present application discloses the use of this multidirectional capability for a number of other diagnostic studies for which digital rectilinear scanners have not been used.

These studies are used to generate images of specific bodily tissue and organs as well as provide quantitative information regarding the volume of organs, tissue density, bone turnover rate, and organ studies such as thyroid uptake. Each study performed by the scanner is controlled by a software package designed for that study.

The present invention also incorporates the use of a laser, or other light source or some mechanical means for identifying a specific portion of tissue being scanned. The user can record a position of particular interest relative to the scan being conducted using the laser. The software can then analyze detected characteristics of the tissue for the identified region of interest.

The scanner assembly also incorporates sensors that detect any obstruction to the movement of the detector during scanning, or during rotation of the scanner assembly. These sensors either deactivate the motor drive thereby stopping any further motion, or they actuate an alarm to inform the operator of some obstruction. This reduces the risk of injury to the patient or damage to the system during operation.

A separate table is used to support the patient so that any region of the body can be positioned within the scanning area of the device. One embodiment utilizes a detector that is rotatable to permit emission studies to be performed on a person in a sitting or supine position.

Emission studies utilize a zoom capability of the detector to obtain images of different focal planes within the tissue being imaged.

The above and other features of the invention including various novel details of construction and combinations of parts will now be more particularly described with reference to the accompanying drawings and pointed out in the claims. It will be understood that the particular multidiagnostic rectilinear scanner systems embodying the invention are shown by way of illustration only and not as a limitation of the invention. The principles and features of this invention may be employed in varied and numerous embodiments without departing from the scope of the invention.

DETAILED DESCRIPTION OF THE INVENTION

Existing rectilinear scanner assemblies used for the in vivo diagnosis of bodily tissue generally permit only uniplanar directional scanning of patients for only one type of study, i.e. either emission with a radionuclide or transmission with a dual energy radioactive source. The following discloses the first multi-diagnostic rectilinear scanner that can conduct a variety of scans on one portable system.

Dual photon absorptiometry with the scanners described herein has the capability to both quantitate and image all kinds of bodily tissue, not just bone density as described in the parent application referenced above. The present application describes the many different diagnostic tools for which absorptiometry from a dual energy radioactive source can be utilized.

The rectilinear scanner is also easily adapted to perform emission studies as well as the use of an x-ray source and detector to perform both transmission and fluorescence radiography studies.

Figure 1:
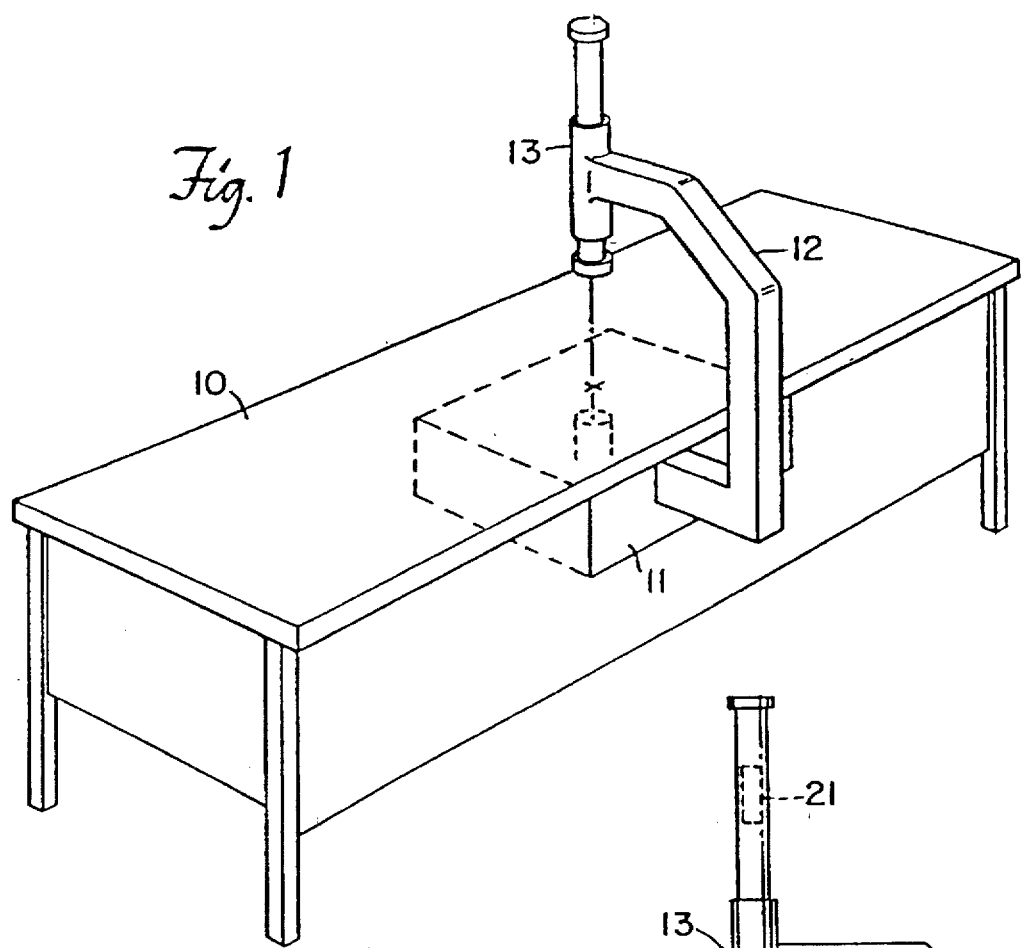
FIG. 1 is a perspective view of a preferred embodiment of the present invention.
Figure 2:
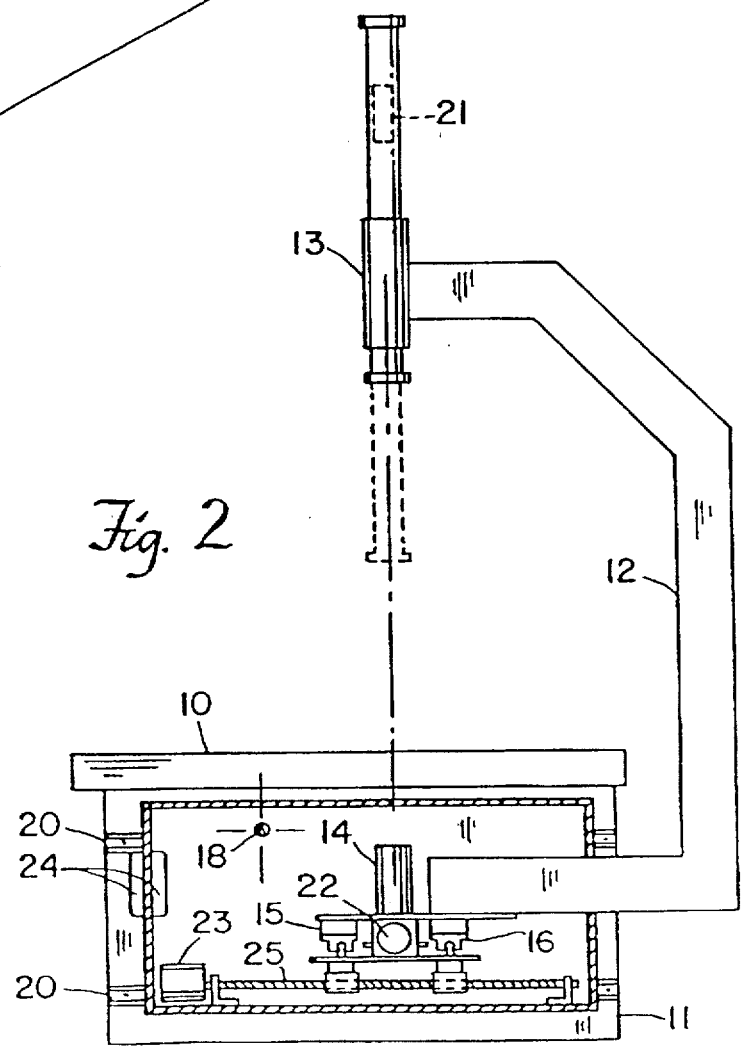
FIG. 2 is a cross-sectional view of the radiation source and detector of FIG. 1 for scanning in the anterior position.

A rectilinear scanner used in a number of diagnostic applications is illustrated generally in FIG. 1. A table 10 on which the patient lies has a drawer assembly 11 which is pulled out from under the table on the side from which a bracket 12 protrudes. The bracket 12 extends in a "C" shape from the drawer assembly 11 to a detecting apparatus 13. FIG. 2 shows, in a cross-sectional view, the relationship between the detector apparatus 13 and the contents of the drawer assembly 11.

A radiation source 14 is mounted on a moveable platform 15. The source 14 is rigidly aligned with the detector apparatus 13 by bracket 12 to insure that radiation emitted from the source is received by the detector regardless of the angle to which the source-detector axis is rotated. The source 14 may be either a dual energy radioactive source or a dual energy x-ray source depending upon the type of study being conducted. The entire rotatable apparatus is mounted on a tray assembly 17. The tray 17 is rotatably mounted onto the assembly plates 19. The plates 19 in one embodiment constitute the side walls of a drawer which compactly houses the source and scanning apparatus.

Figure 3:
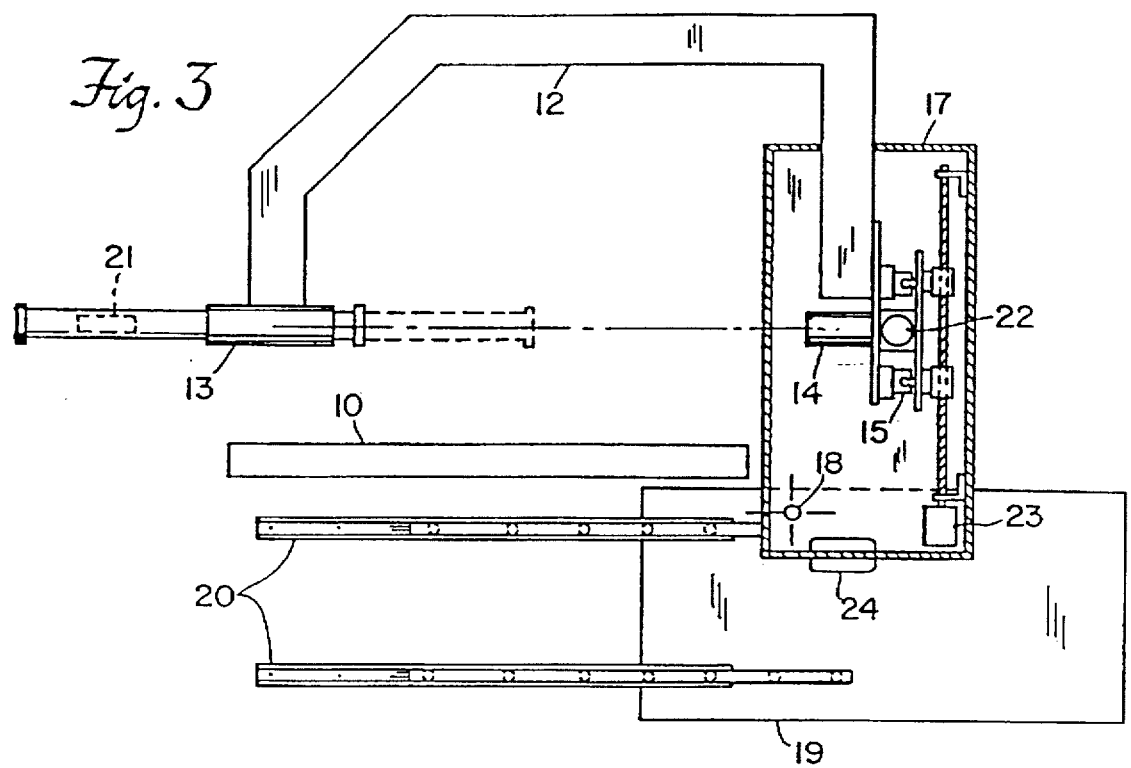
FIG. 3 is a cross-sectional view of the apparatus of FIG. 1 rotated to the lateral position.

To rotate the apparatus from the anterior position shown in FIG. 2 to the lateral position shown in FIG. 3, the following steps must be taken. The user releases a locking mechanism and pulls the arm horizontally to one side of the table so that the tray 17 and plates 19 slide the source from under the center of the table to avoid contact with the table during rotation. In one embodiment of the invention the source is approximately one inch below the table during anterior scanning and thus cannot be rotated without lateral movement. Source proximity to the table is desirable, as the source and detector are preferably as close to one another as possible to yield the best possible image. The drawer assembly plates 19 telescope out along the glides 20 until the pivot point 18 is astride the table 10. The plates 19 are then locked in position by a locking mechanism (not shown). The arm 12 and the attached source and tray assembly 17 are rotated manually by the user about the axis 18 to the desired position. Note that the pivot axis location must be chosen so that the source and scanning apparatus are rotated into a position just above the plane of the table. This insures that objects positioned on the table can be fully scanned laterally. The pivot location also affects the adjustment of the center of gravity as discussed below. In an alternative embodiment of the invention, the lateral movement of the drawer assembly and/or the rotation may be automatically controlled by adding the necessary motor and control systems. Such an embodiment is described below with reference to FIGS. 6–8 where there is a stationary axis of rotation.

FIGS. 2 and 3 also illustrate the presence of weights 21 and 24. After initial assembly of the apparatus, the center of gravity of the rotating elements must be adjusted to assure ease of manual rotation. In a preferred embodiment of the invention, the center of gravity of the rotating elements is located along the pivot axis 18. When the center of gravity is so situated the rotating elements will not accelerate under their own weight when the bracket 12 is rotated to any chosen angle, stopped and released.

Figure 4:
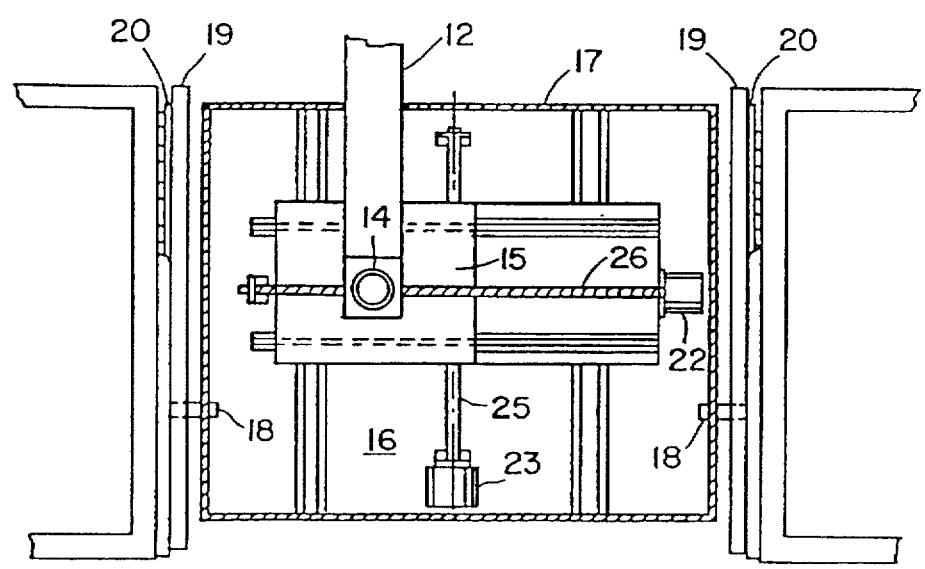
FIG. 4 is a top sectional view of the drawer assembly.

FIG. 4 shows a top view of the drawer assembly 11 and illustrates the location of the pivot axis 18, the glides 20 for displacement of the plates 19, and the tracks 26 on which the platform 15 rides. The platform 15, as well as the attached source 14, bracket 12, and detector apparatus 13, are moved in a plane perpendicular to the source-detector axis. The driving mechanism for the scanning motion is a so-called "x-y" table 16. The scanning mechanism is comprised of threaded bars, one running along the longitudinal or "y" axis 26 of the table, the second 25 running perpendicular to the first across the width or "x" axis of the table. The platform 15 has threaded housings which receive, and are driven by, the two threaded bars. The threaded "x" bar 26 is rotated by the motor 22. When the scanning assembly is rotated along with the source and detector, this insures full scanning capability at any angle. In a preferred embodiment of the invention, the scanning mechanism is controlled automatically by feeding the scanning rate and the size of the area to be scanned into a computer, which then triggers the radiation source and coordinates the desired scan. The data received by the detector can be processed, stored, or used to provide images of the tissue under study.

During initial rotation of the system from the vertical position, the weight of the tray assembly 17 and enclosed elements controls the balancing of the bracket 12 and the attached components. The weights 24 are added to the front wall of the saddle to adjust the center of gravity in the horizontal plane. The weight 21 is added to the detector system to adjust the center of gravity in the vertical plane. As the system is rotated through larger angles from the vertical (e.g. 45°–90°), the correct weighting of the bracket and detector by weight 21 becomes more important to maintain ease of manual rotation.

By rotating the detector arm, scanning of the lumbar spine in both the anterior and lateral projections is now possible without repositioning the patient. The patient remaining in the supine position for both the lateral and anterior-posterior projection maintains the correct alignment of both projections, permits direct correlation of the two studies, and anatomically is diagnostically correct.

Performing the lateral image as the first study may enable the physician to observe extra-osseous calcification in tissue overlaying the lumbar spine. In the anterior-posterior projections, such extra-osseous calcification cannot be distinguished from bone, and could therefore interfere with accurate bone density measurements in that projection. The bone being studied may be examined in real time by amplifying the signal output from the detector and displaying the black and white or colored image on a screen or printing the image on film using as many as 64 shades of gray to obtain a highly detailed image.

Figure 5A:
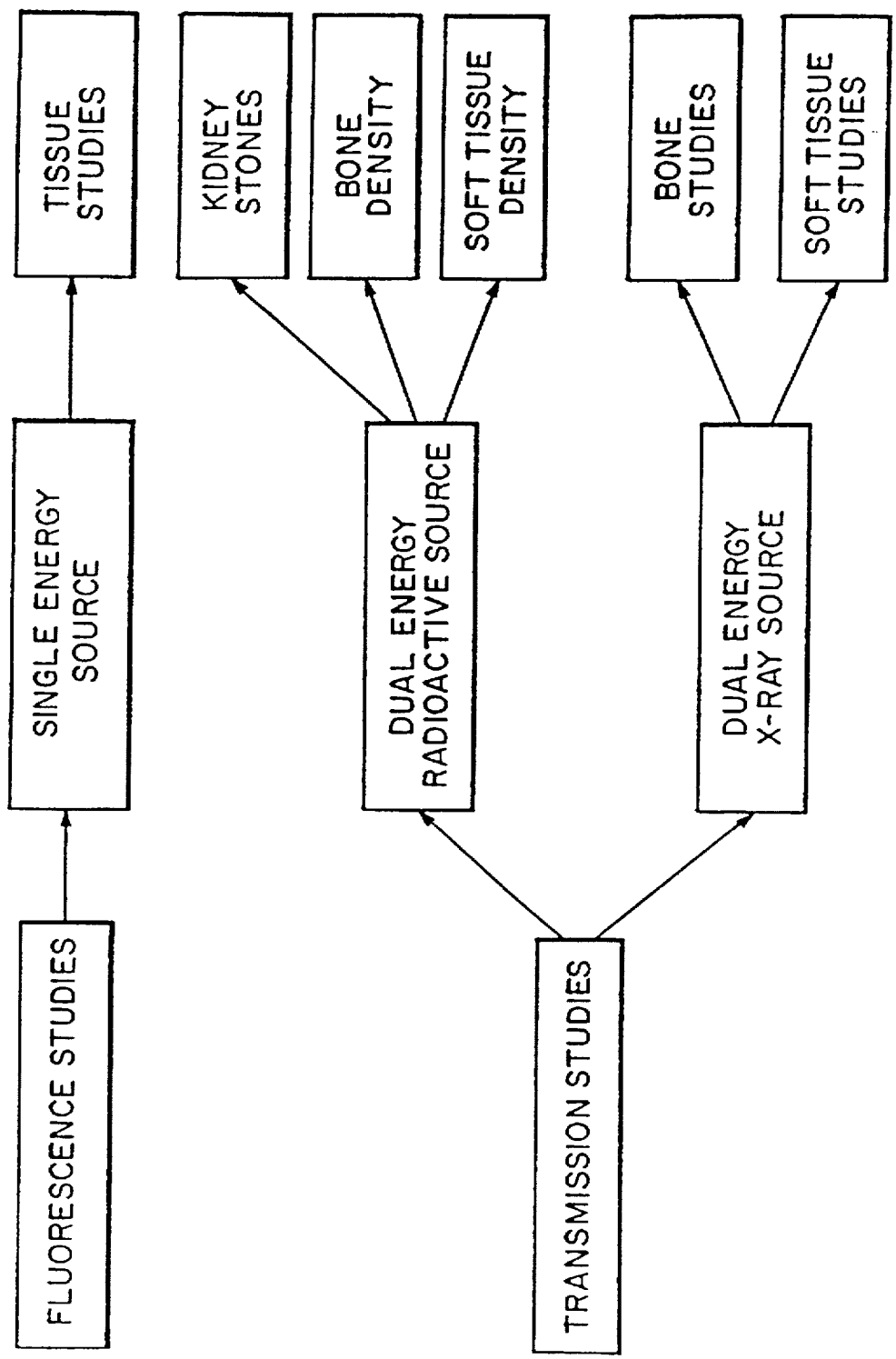
FIGS. 5a and 5b schematically illustrate a number of diagnostic scans that can be conducted with the rectilinear scanner of the present invention.
Figure 5B:
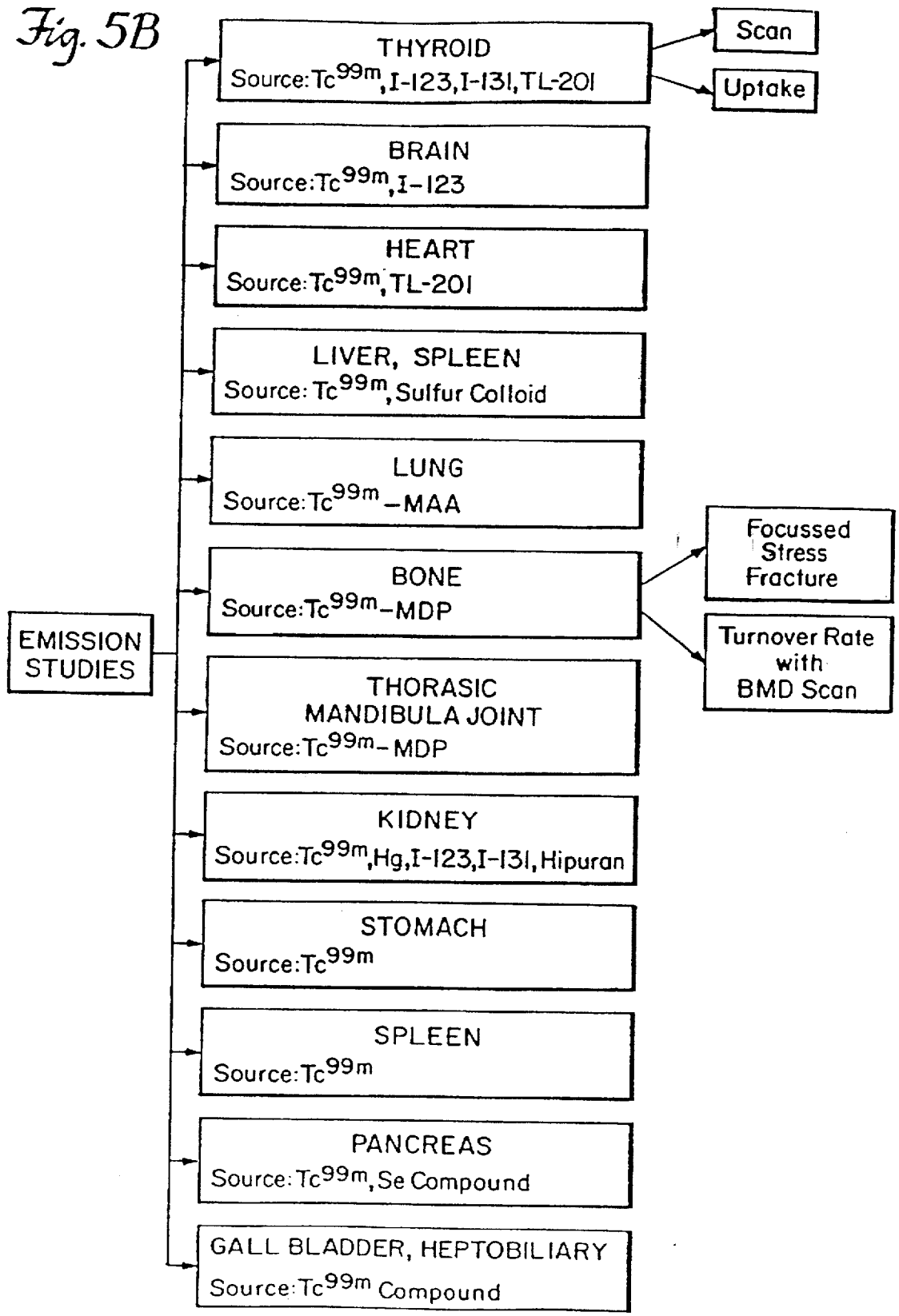

FIG. 5a illustrates the types of transmission and fluorescence studies that can be performed using the scanner. The system can further be used for performing traditional thyroid scans which are useful in the diagnosis of a number of thyroid conditions. As shown in FIG. 5B, numerous emission studies can be performed on the present system including the performing of thyroid uptake tests that are normally performed on a so-called "uptake unit." This test is used for diagnosing the glandular disorder of hyper-or hyothyroidism. The thyroid scan and uptake test typically uses a thyroid scan and an orally administered dose of a radioiodine. The iodine is actively trapped and organified in the thyroid gland. The amount of the radioiodine appearing in the thyroid gland at 12–24 hours after administration is an index of the rate of thyroid hormone production.

The system can further be used for the detection of stress fractures that are currently detected on gamma camera systems. By injecting technetium –99 m labelled methylene diphosphate (MDP), stress fractures located within a skeleton can be detected and a static image generated. The higher resolution of digital rectilinear scanners is particularly important for this measurement. The system utilizes a zoom imaging feature for the close examination of the area under study. Other emission studies including those for the brain, heart, liver, lung, kidney, stomach, spleen, pancreas and gallbladder are all depicted in FIG. 5b. The types of radioisotopes typically used for these studies are also indicated.

Figure 6:
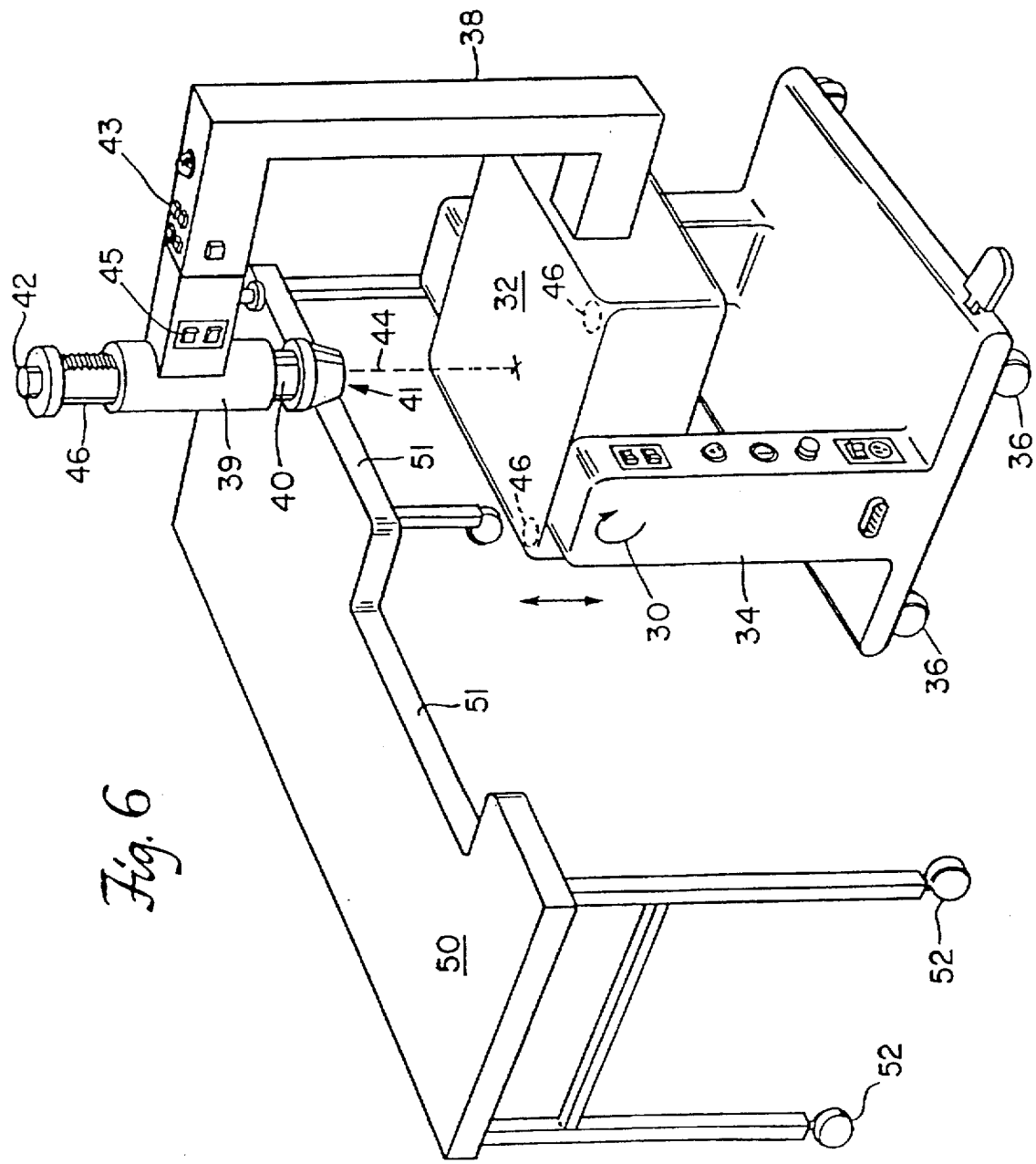
FIG. 6 is a perspective view of a preferred embodiment of the invention having a single axis of rotation along with a separate table used in conjunction therewith.

Another preferred embodiment of the invention is depicted in the perspective view of FIG. 6. This system has a single axis of rotation 30 where the scanner cradle 32 rotates in the direction indicated to perform non-anterior scans.

Figure 7:
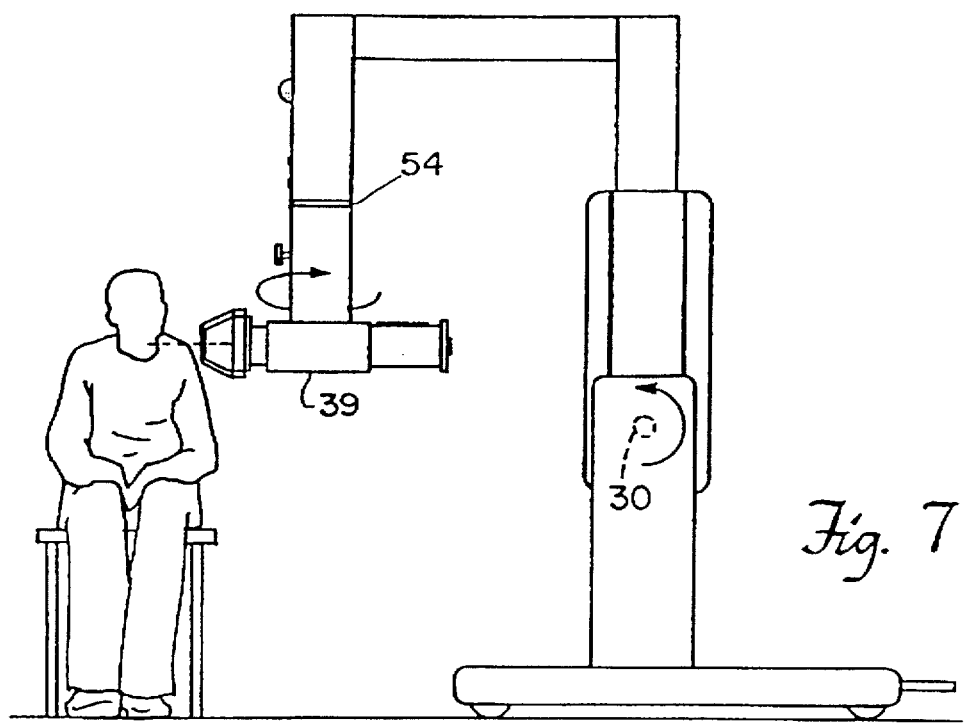
FIG. 7 is a side view of the embodiment of FIG. 6 illustrating the rotation of the detector to enable the performing of emission studies on a sitting patient.

The patient is placed on a separate moveable table 50 having wheels 52 to permit easy positioning of the area to be scanned relative to the source detector axis. Alternatively, as shown in FIG. 7, the scanner can rotate about axis 30, and the detector mount 39 can be rotated at pivot point 54, to permit emission studies to be performed on a patient in the sitting position.

Figure 8:
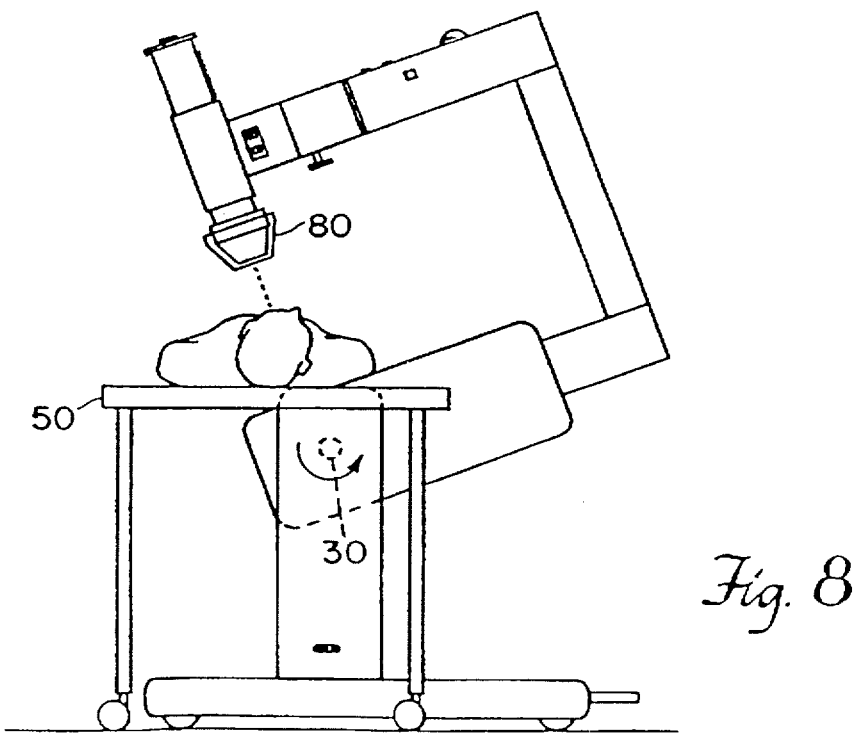
FIG. 8 is a side view of the scanner assembly of FIG. 6 that has been rotated to perform a study at an oblique angle.

The table 50 also has two rectangular notches 51 along one side. Each notch or recess 51 is dimensioned to permit the scanner cradle 32 to be inserted into the notch when the cradle 32 is partially or totally rotated. This permits the easy positioning of the area to be scanned, particularly during scans at oblique angles. FIG. 8 illustrates the nestling of the cradle 32 into either recess 51.

The scanner cradle 32 is supported by a base 34 mounted on wheels 36. The cradle 32 contains an x-y table similar to that shown in FIG. 4. The cradle 32 also contains a dual energy radioactive or x-ray source, depending upon the type of study being conducted. For emission studies a shutter exposing the source is automatically closed. Fluorescence studies are also conducted wherein a dye introduced into the tissue of interest, or the tissue itself, is made to fluoresce upon the suitable irradiation of the tissue. The software system can be programmed to open the shutter only while transmission and fluorescence studies are being conducted.

The adjustable detector 40 mounted at the end 39 of the arm 38 is fitted with a light source 46 such as a laser operated by switch 42 which generates a beam 44. The laser 46 or some other mechanical indicator permits the operator to locate the point under study at any time before, during or after the study. This is particularly useful for the physician who wishes to examine a particular portion of tissue. By centering the light source over the portion of interest, the operator can then record the location by momentarily actuating the switch 42. The system software will then record that point relative to the entire scan that has been, or will be taken. The indicator can be used in conjunction with both transmission or emission studies. The operator can easily maneuver the arm 38 by directional switches 43. Switches 45 operate to lower or raise the detector 40 in telescoping fashion.

Alternatively, an image of the area under study can be generated on a monitor and points or regions of interest may be identified which may not be palpably or visually detectable. The software is then used to "label" or "mark" this region or a number of such regions on the screen. On command, the software can direct the detector to move over the precise point of the anatomy which has been identified on the monitor.

Figure 15:
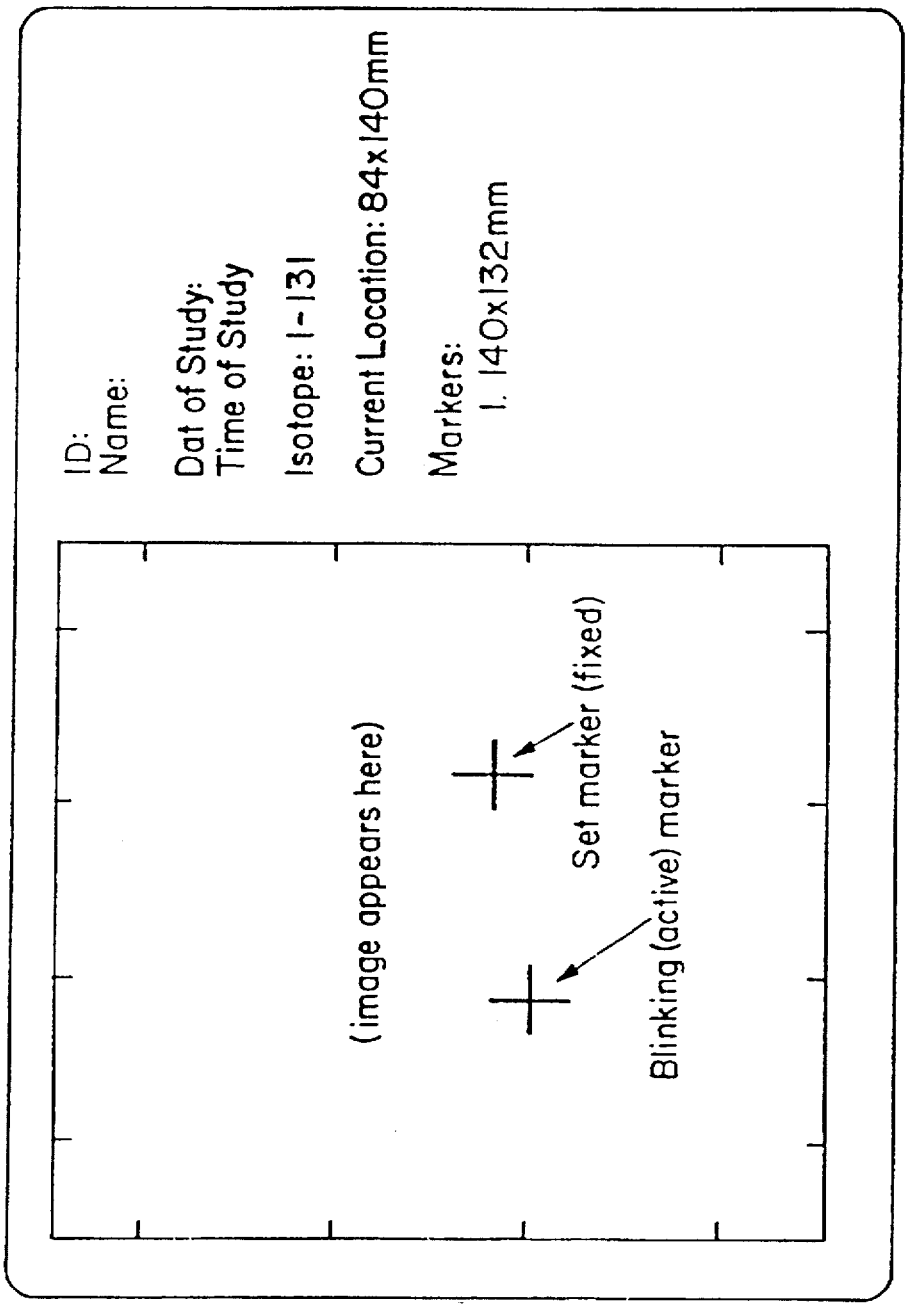
FIG. 15 illustrates the imaging employed for marking and recording points of interest.

A laser beam can now be used to illuminate the point identified on the monitor and the user can mark the point on the patient's skin with a dye marker. FIG. 15 shows an image in which a marker has been set and listed as a recorded marker. A blinking marker designates the current location of the laser. The image on the screen can also be printed on film with the point marked by the laser appearing as a white crosshair, thereby identifying the precise anatomical location.

If the physician seeks to scan an area he believes to be abnormal, he first identifies the area by palpating the tissue with his fingers and marking the point either by the laser, or first with a pen or dye and then recording the point with the laser. An x-ray image can then be produced, for example, with a white crosshair marking the point of interest on the screen or the film.

Figure 16:
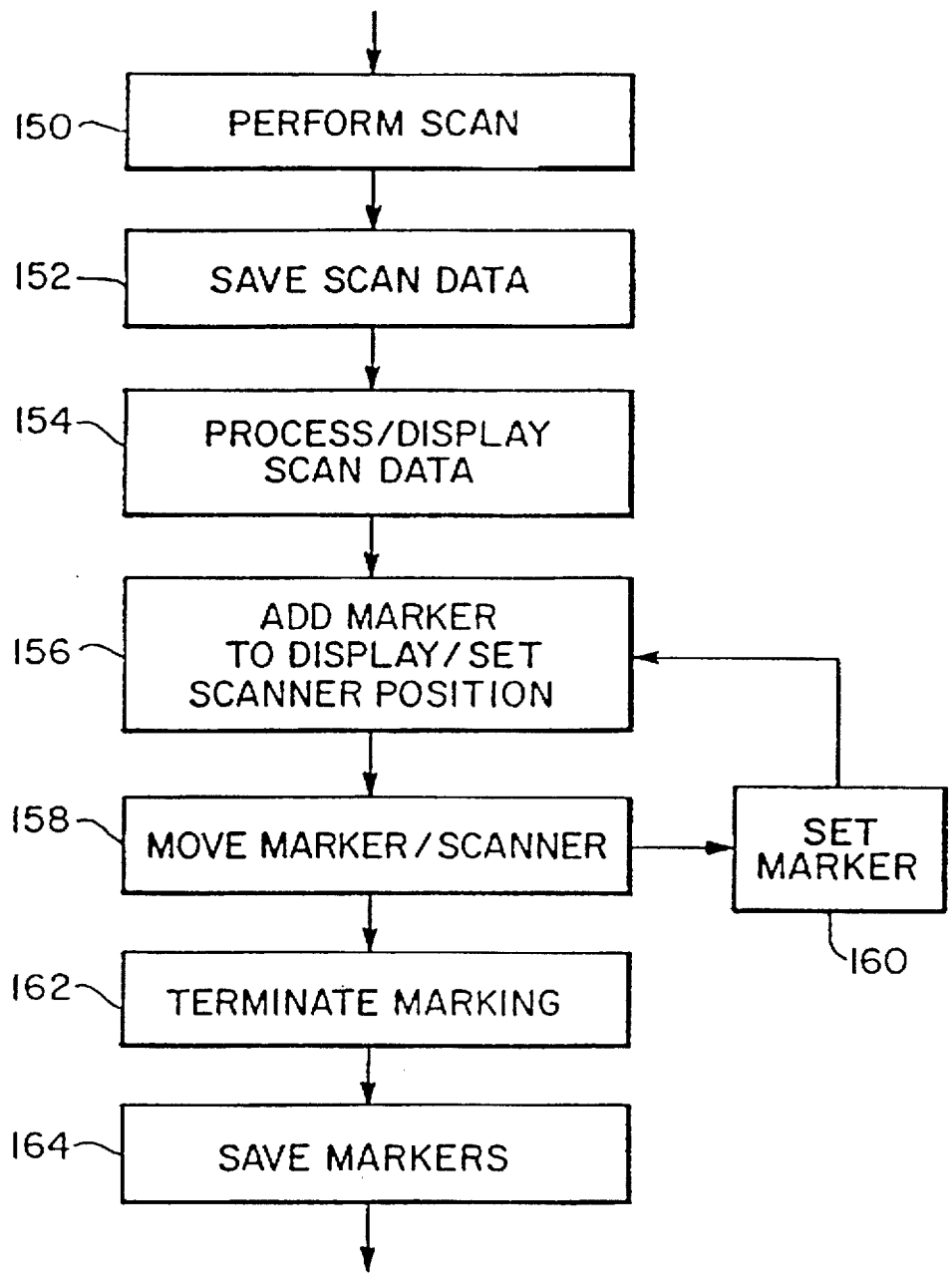
FIG. 16 illustrates a processing sequence used in marking the points of interest.

The software for the laser marking system can have the processing sequence illustrated in FIG. 16. In this sequence a scan 150 has been performed, the data stored 152 and then processed and displayed 154. A marker can then be added to the displayed image 156 and the marker is moved 158 to the proper position over the point or region of interest. The position is then marked 160 and further markers can then be added and recorded until the process is terminated 162 and one or more markers are permanently stored 164.

Figure 9:
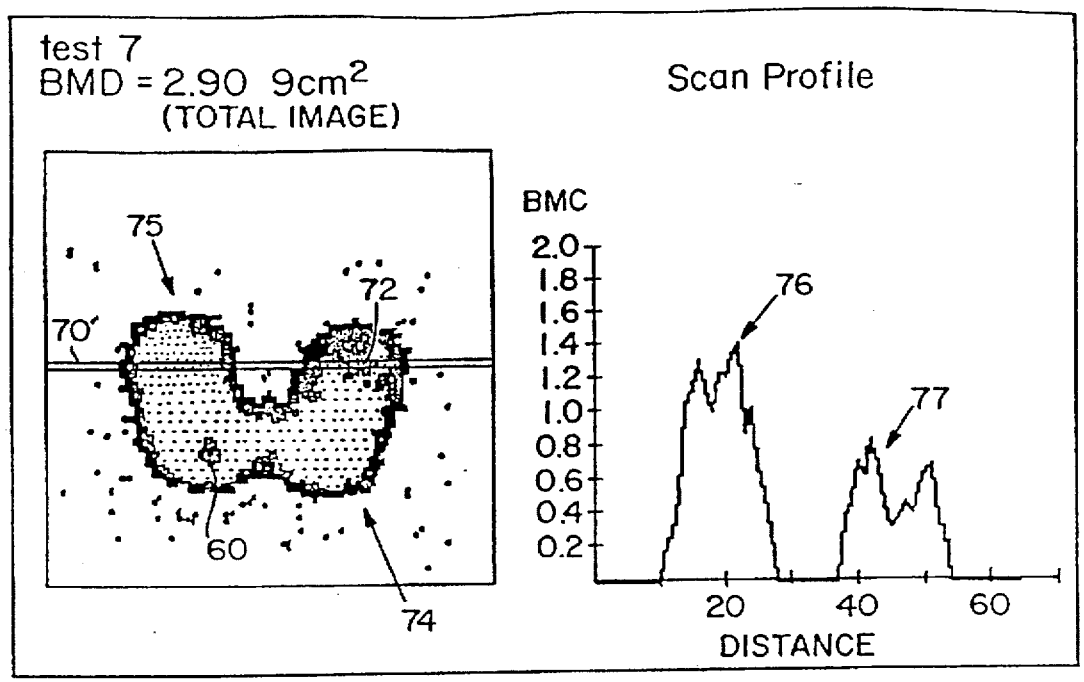
FIG. 9 is an illustration of an image generated from a thyroid uptake procedure and a graphical representation of a measured characteristic of the tissue.

FIG. 9 illustrates the results of such a scan for a thyroid uptake. If a physician were to feel a particular nodule as a result of a physical examination of the thyroid, the nodule could be identified using the laser 46. The scan results could then establish whether a "hot spot" 60 of the scan corresponds to the nodule formerly "labelled" by the laser. A horizontal slice 70 is selected across the image of the thyroid. The number of counts for the slice is then graphically displayed as a function of position. The hot spot 72 on the right side 74 of the image generates a substantially larger peak 76 then the peak 77 for the left side 75 of the image.

Figure 10:
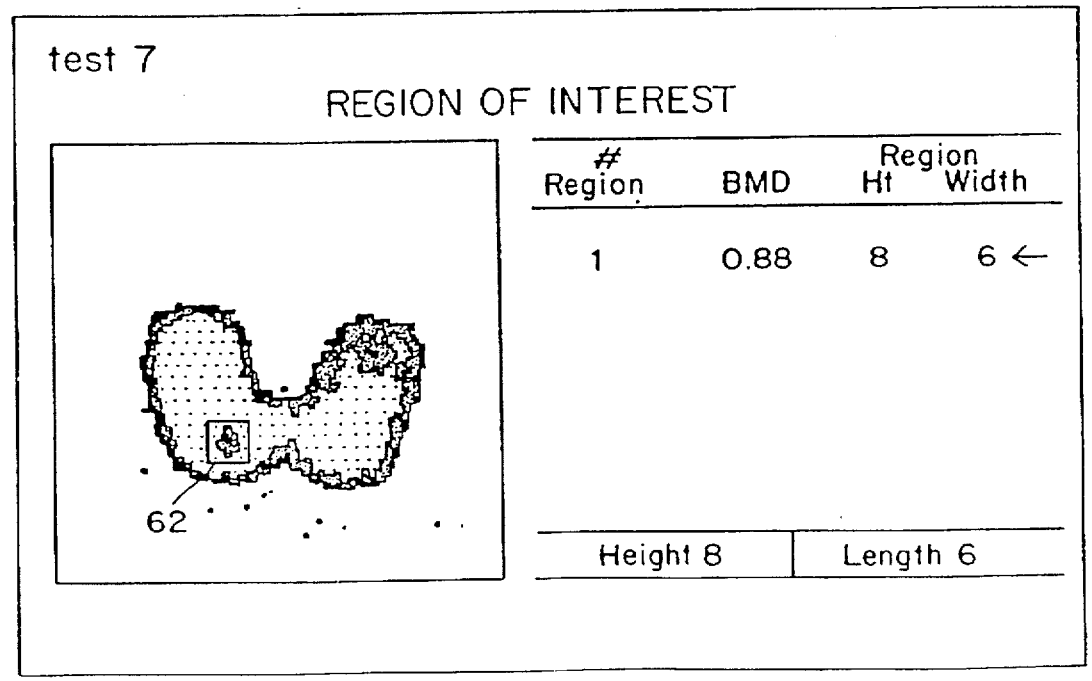
FIG. 10 is another illustration of an image generated wherein a particular region of interest has been selected and a characteristic thereof listed in tabulated form.

FIG. 10 further illustrates how a rectangular portion 62 can be selected such that a region of interest therein can be specifically studied. The image shown is the result of a thyroid uptake using the system in FIG. 6.

The height and length of the region can be selected by the operator and the count within the region can be calculated by a subroutine and displayed on a table adjacent the image being analyzed. A number of such regions can be sequentially defined analyzed, and displayed.

Figure 11:
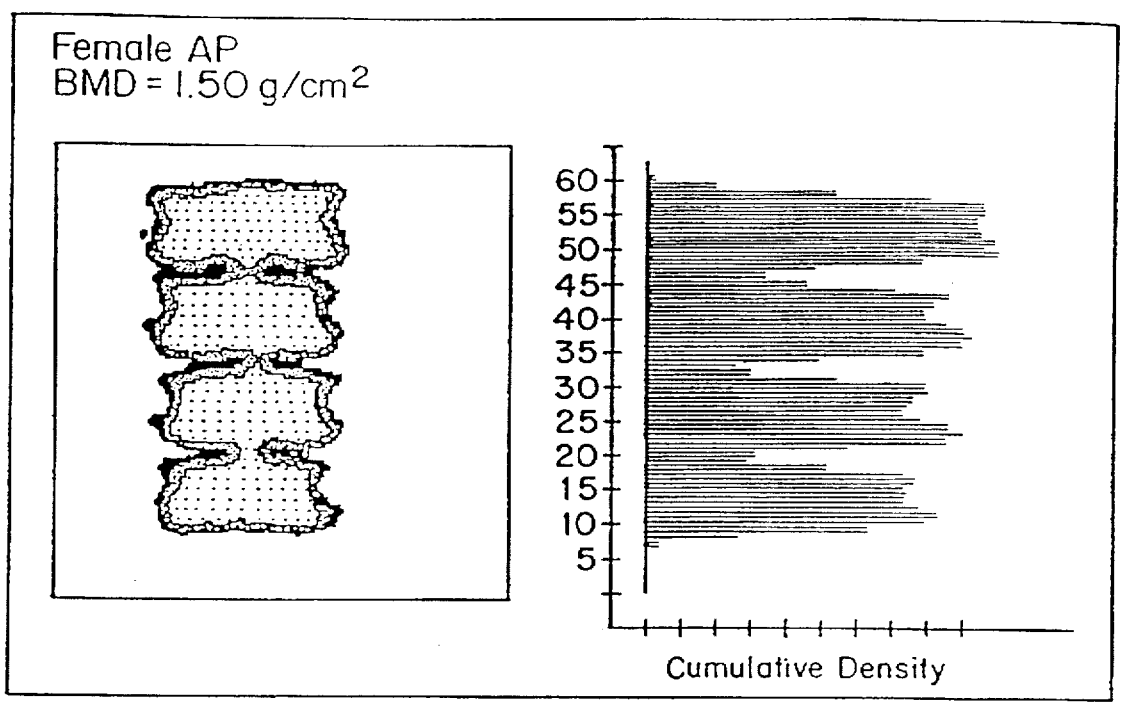
FIG. 11 is an illustration of an image generated from a bone densitometry study along with a graphical illustration of the quantified cumulative density.
Figure 12:
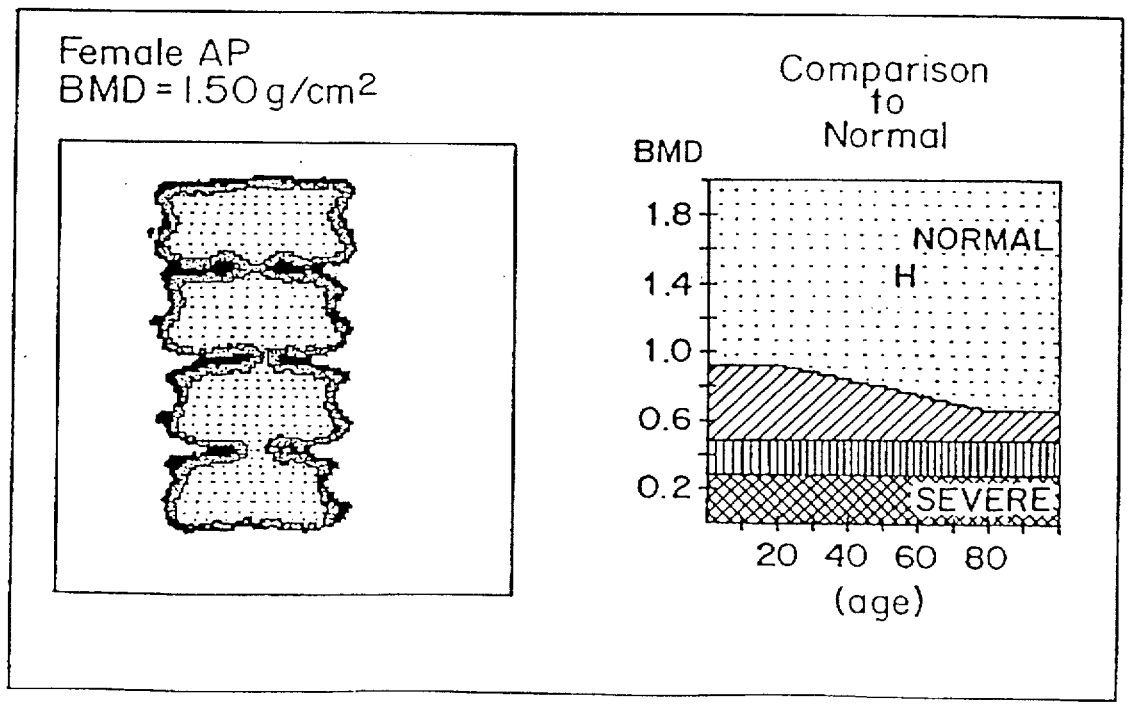
FIG. 12 illustrates an image similar to that shown in FIG. 11 along with a graphical depiction comparing the results of the scan to a norm.

FIGS. 11 and 12 illustrate the imaging of bone density studies along with graphical analyses showing cumulative density as a function of position and the comparison of acquired data relative to stored normative values.

The table 50 on which the patient lies permits the cradle 32 to rotate under or astride the table 50 so that studies can be conducted at any number of angles. Lateral imaging can be conducted by rotating the cradle so that the source detector axis is positioned above the table 50.

A preferred embodiment of the invention incorporates safety features that warn the operator of potentially dangerous situations where the patient may be injured or the system damaged as a result of the automatic movement of the detector assembly during the positioning or scanning thereof, or due to the rotation of the scanner cradle 32. The end 41 of the detector that receives radiation from the source is fitted with a spring mounted cone 80. If there is some obstruction of the receiving end 41 of the detector the cone 80 is displaced relative to the receiving end 41 causing the actuation of an electrical circuit within the controller 82 resulting in the shutdown of the motor drive within the cradle 32.

The upper surface 45 of the cradle 32 is spring mounted such that if the cradle 32 encounters some obstruction during rotation, such as the table 50, the surface 45 is displaced causing the actuation of a second alarm circuit 56. The circuit 56 will trigger an audible alarm to notify the operator and can optionally result in the shutdown of the drive motor that rotates the cradle 32.

The rotating scanner assembly on the PolyScan diagnostic system includes the scan drive table and a lead-shielded detector tube weighing about 100 pounds. It may be rotated from −30 deg to +90 deg to perform scans at different angles. The rotation mechanism includes heavy duty gears driven from an electric motor through a reinforced rubber belt with teeth, referred to as a timing belt. Due to the weight of the rotating assembly a simple mechanism has been incorporated that senses loss of tension in the belt in the event of belt failure and locks to prevent further rotation.

The system consists of two spring loaded pawls that engage and stop the main gear from turning in case of a failure of the belt. The tension of the belt in normal operation holds the pawls away from the gear unless the belt breaks. Strong springs will drive the pawls into the teeth of the gear if the belt tension is lost, stopping all gear motion almost instantly.

Figure 13:
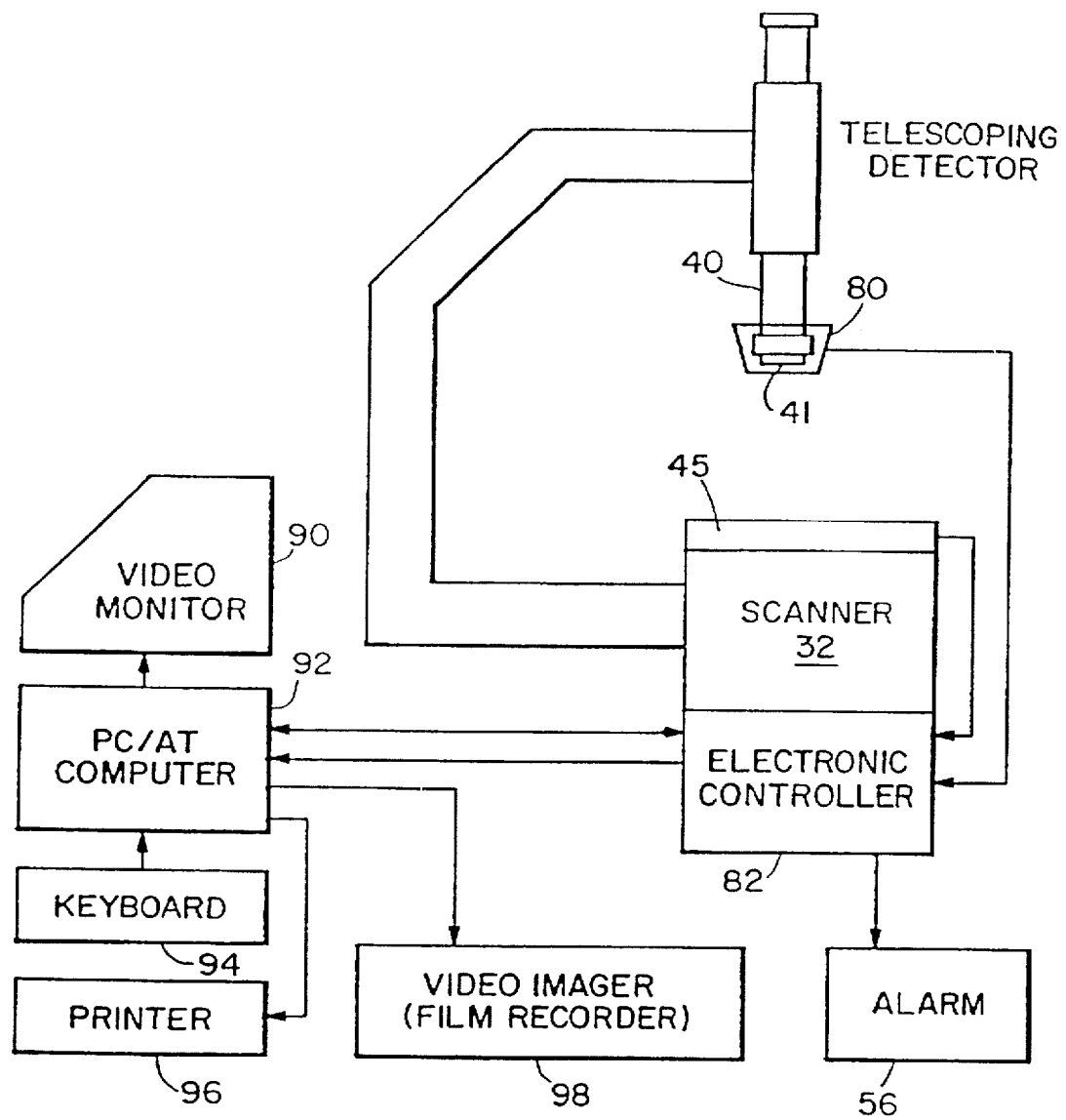
FIG. 13 is a schematic diagram illustrating the control system for the embodiment of FIG. 6.

A schematic diagram of the system is shown in FIG. 13 showing the relationship between the control circuitry 82, the cone 80, the surface 45 of cradle 32 and the alarm 56.

The controller 82 is interfaced with a computer 92 which processes the information generated by the detector 40 and generates an image on the monitor 90, a color print on printer 96, or a film on the film recorder/video imager 98.

Figures 14, 14A:
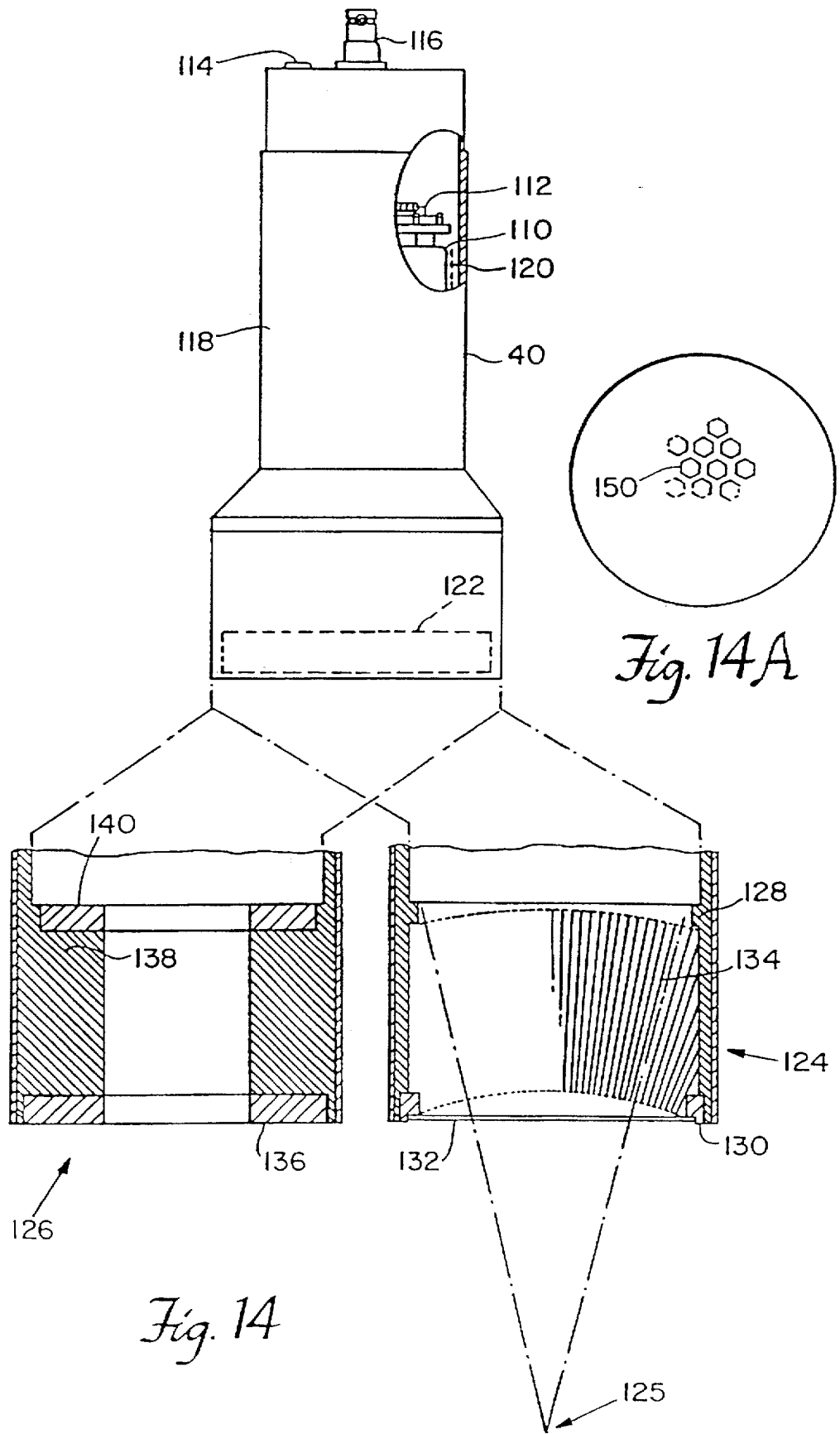
FIG. 14 is a partially sectioned view of the detector assembly and the collimators used in conjunction with the performing of transmission and emission studies.
FIG. 14A is a partial cut away top view of the focusing collimator shown in FIG. 14.

FIG. 14 illustrates the detector 40 along with two types of collimators used in conjunction therewith. The detector 40 has a sodium iodide crystal 122 coupled to a collimator on one side and a photomultiplier tube 110 on the opposite side. The tube 110 is surrounded by an internal radiation shield 120. The outer surface 118 is preferably a light aluminum shield. An adjustable gain potentiometer 114 is positioned adjacent a connector 116 on top of the detector 40. Not shown in this figure are the means for telescoping the detector relative to the arm 38.

The two collimators 124 and 126 are used for performing emission and transmission studies respectively. A third type of collimator similar to 126 is used for thyroid uptake studies without the lead rings 136 and 140, and without the spacer 138 separating the rings. The angled columns 134 of collimator 124 transmit light from a point 125 lying within a focal plane that is scanned by the detector. By telescoping the collimator 124 relative to arm 38, the focal plane of the collimator can be vertically repositioned between scans. This permits the obtaining of an image along a number of slices of the tissue intersecting the focal plane. A lead ring 130 defines the aperture of the collimator 124 which is covered with a thin aluminum plate. All three collimators incorporate an inner wall 128 which prevents stray radiation from penetrating into the detector 40.

The ability of the system to scan along different focal planes provides the capability for characterizing tumors in patients. As the image created can be scaled to a one-to-one correlation with the tissue being scanned, the geometry of the organ or tissue can be accurately measured. For example, the size of a tumor and the depth of the tumor within the patient can be determined using the focusing collimator to scan at different planes within the body. These measurements can be performed at different angles without moving the patient. By identifying the location of the tumor at each angle with the on screen "marker" the tumor depth location can be determined from the intersection of the lines generated at each angle.

Repeat studies of the same region of interest can be performed to monitor any change in condition. The patent is positioned relative to the scanner assembly to reproduce the conditions of the original study. The original points of interest that were marked on screen or identified by the laser and stored in the system memory can be scanned and the results compared with prior studies.

FIG. 14A is a partial, cut away top view of the angled column structure 134 showing the six sided shape of each column which are separated by a thin wall 150.

Figure 17:
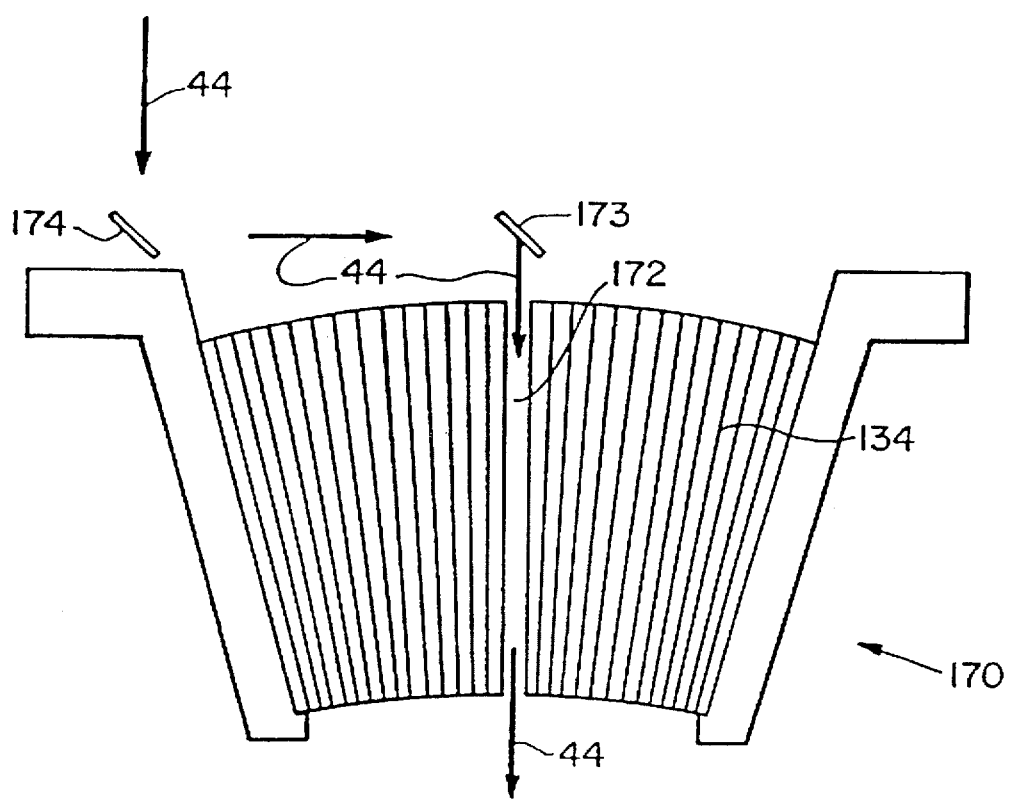
FIG. 17 is a cross-sectional view of another preferred embodiment of a collimator used for performing simultaneous emission and transmission studies.

FIG. 17 shows another preferred embodiment of a collimator 170 that can be used to perform simultaneous emission and transmission studies. Collimator 170 has a cylindrical column or aperture 172 extending through the center such that radiation transmitted from a source and directed through the object being scanned passes through aperture 172 onto the detector. The diameter of the aperture is generally in the range between 3 and 10 millimeters but is not limited strictly to these dimensions. Note that transmission radiation passes through the angled columns 134 of collimator 170 as well as the aperture 172.

Generally in most simultaneous emission and transmission studies the number of transmission counts greatly exceeds the number of emission counts. The software can be used to correct for the difference between the two studies so that the results of each study can be compared on the same scale.

Performing simultaneous emission and transmission scans generally results in three different energy levels being acquired by the detector. Two energy levels arise from the dual energy source used for the transmission study.

A third energy level arises from the injected radioisotope used in the emission study. A multichannel analyzer used in conjunction with the detector can be used to count each energy level through one scan. Alternatively, two scans could be used to acquire all three energy levels.

Note that the aperture 172 can also be used to allow the laser beam 44 to pass through the collimator assembly to identify and record a region of interest. Reflective surfaces 173 and 174 can be used to direct the beam 44 to the center of the collimator 170 and through aperture 172.

Figure 18:
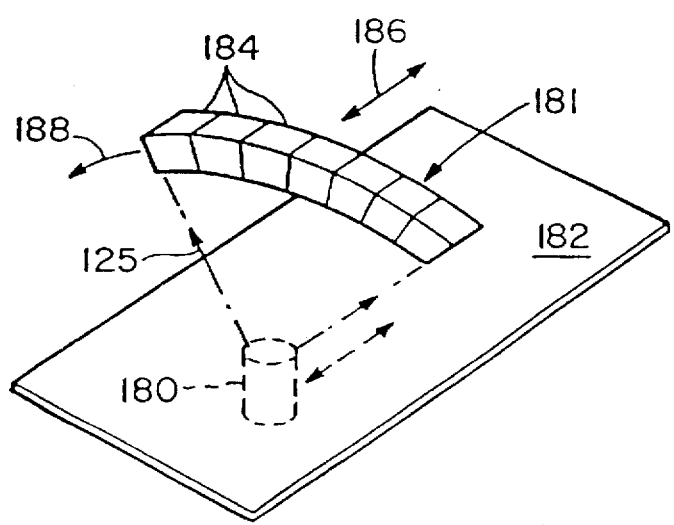
FIG. 18 is a schematic perspective view illustrating a preferred embodiment utilizing a fan beam and a linear array of detectors used to perform linear scans.

Another alternative embodiment is shown in the schematic perspective view of FIG. 18 wherein a source 180 and a detector assembly 181 are translated along either longitudinal direction 186 relative to the table 182 which supports the object being scanned. The detector assembly 181 is comprised of a number of individual detectors 184 assembled in an arced linear array. The detectors 184 sense radiation 185 projected from source 180 in the form of a fan beam without the rectilinear motion described in earlier embodiments. This embodiment can utilize the digital processing and imaging systems previously described and the detector and source can be rotated in direction 188 to perform oblique and lateral studies similar to those described in conjunction with earlier embodiments.

Figure 19:
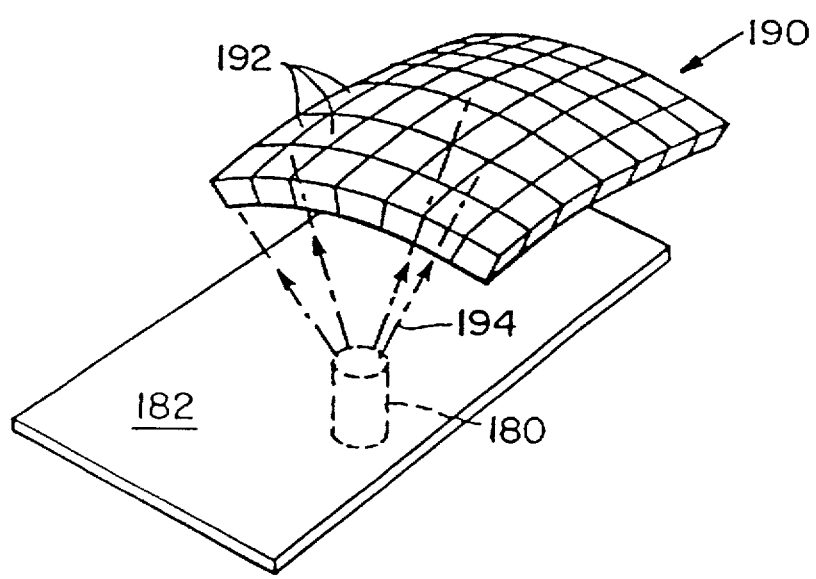
FIG. 19 is a schematic perspective view of another preferred embodiment utilizing a two dimensional array of detectors to perform studies at different angles relative to the object being scanned.

Another preferred embodiment is illustrated schematically in FIG. 19 where a stationary source 180 underneath table 182 projects radiation 194 in the shape of an inverted cone onto a two dimensional detector array 190 comprised of a number of individual detectors 192. Each detector 192 is preferably positioned at the same distance from the radiation source 180. Although the source 180 is stationary during the performance of each study, it rotates in conjunction with the detector 190 to perform oblique and lateral studies.

Both of the embodiments shown in FIGS. 18 and 19 are used to perform both simultaneous transmission and emission studies as described in connection with earlier embodiments.

While the invention has been particularly shown and described with reference to preferred embodiments thereof, it will be understood by those skilled in the art that various changes in form and details may be made without departing from the spirit and scope of the invention as defined in the appended claims.

We claim:

1. A method of scanning the spinal column of a patient comprising:

positioning a human patient on a support surface, the spinal column of the patient extending along an axis of the support surface;

providing a C-shaped member mounted relative to the support surface, the C-shaped member rigidly aligning an x-ray radiation source and a detector array and being selectively driven in a first direction along the axis of the support surface by a scanning motor, the x-ray radiation source and detector array being aligned in a plane that is transverse to the axis of the support surface, said detector array being elongated in a direction conforming to said plane;

providing a data processor for controlling the scanning motor and a memory for recording data;

scanning a region of a patient's spinal column at a first angle with the C-shaped member, x-ray source and detector array to detect radiation at two energies with the detector array that is transmitted through the region from the source while the C-shaped member is being driven along the axis of the support surface by the scanning motor;

rotating the C-shaped member, the x-ray radiation source and detector array about the support surface to a second angle with a motor such that the source and detector array are aligned through the spinal region at a second angle different from the first angle;

scanning a region of the spinal column with the C-shaped member, x-ray source and detector array, the detector array receiving radiation from the source that is transmitted laterally through the region to the detector array at the second angle while the C-shaped member is being driven along the axis of the support surface by the scanning motor;

determining bone density in the spinal column from radiation detected with the detector array at two energies transmitted through the spinal column during the scanning at least at one of the first angle and the second angle; and generating an image of the scanned region of the spinal column on a display with radiation detected by the detector array.

2. The method of claim 1 further comprising providing a second motor to drive the C-shaped member in a second direction that is perpendicular to the first direction.

3. The method of claim 1 further comprising directing a fan beam of x-ray radiation through the patient during scanning and detecting said fan beam with said detector array.

4. The method of claim 1 further comprising displacing the C-shaped member to one side of the spinal region after scanning at the first angle and before rotating the C-shaped member to the second angle.

5. The method of claim 1 further comprising directing laser light onto the patient to identify a position of the C-arm and recording the position of the C-shaped member relative to the support surface.

6. The method of claim 5 further comprising indicating on the display a position on the patient illuminated with the laser.

7. The method of claim 1 wherein the step of scanning at the first angle further comprises scanning at an oblique angle relative to the support surface.

8. The method of claim 1 further comprising determining a distance of a region within the scanned region of the patient.

9. The method of claim 1 further comprising positioning the x-ray radiation source under the support surface during the scanning at the first angle.

10. A method of scanning a region of a patient's lumbar spine comprising:

positioning a human patient on a support surface, the lumbar spine of the patient extending along an axis of the support surface;

providing a C-shaped member mounted relative to the support surface, the C-shaped member rigidly aligning an x-ray radiation source and a detector array that detects radiation transmitted through the patient at two energies in a vertical plane, the detector array being selectively driven in a first direction along the axis of the support surface by a motor, said detector array being elongated in a direction conforming to said plane;

providing a laser that directs light onto a patient to position the source and detector array relative to the support surface;

scanning a region of the patient's lumbar spine at a first angle with the C-shaped member to detect with the detector array radiation transmitted in the vertical plane through the region from the x-ray radiation source, the C-shaped member being driven by the motor to scan along the axis of the support surface;

rotating the C-shaped member, the x-ray radiation source and the detector array in the vertical plane about the support surface to a second angle such that the source and detector array are aligned laterally through the region of the lumbar spine at an angle different from the first angle;

scanning a region of the lumbar spine with the C-shaped member, x-ray radiation source and detector array such that the detector array detects radiation from the source that is transmitted laterally through the region to the detector array while the C-shaped member is being driven in the first direction along the axis of the support surface at the second angle;

determining bone density in the lumbar spine from radiation detected with the detector array at the two energies transmitted through the lumbar spine during the scanning at least at one of the first angle and the second angle;

generating and displaying an image of a scanned region of the lumbar spine on a display from radiation detected with the detector array.

11. The method of claim 10 including the step of displacing said C-shaped member laterally relative to said support surface in a direction perpendicular to the axis of the support surface, between said scanning at said first angle and the scanning at the second angle.

12. The method of claim 10 further comprising laterally displacing the C-shaped member with a second motor.

13. The method of claim 10 further comprising providing rails to support the C-shaped member relative to the support surface during lateral displacement of the C-shaped member.

14. The method of claim 10 further comprising providing a data processor and a memory in which to record scan data and a position of an illuminated region of the patient upon illumination with laser light.

15. The method of claim 14 further comprising displaying on the display the illuminated position.

16. A method of measuring density in a region of interest in a patient comprising:

positioning a human patient on a support surface;

providing a C-shaped member mounted relative to the support surface, the C-shaped member rigidly aligning an x-ray radiation source and a detector array and being selectively driven in a first direction along an axis of the support surface by a scanning motor, the x-ray radiation source and detector array being aligned in a plane that is transverse to the axis of the support surface, said detector array being elongated in a direction conforming to said plane;

providing a data processor for controlling the scanning motor and a memory for recording data;

scanning a region of interest of a patient at a first angle with the C-shaped member, x-ray source and detector array to detect radiation at two energies with the detector array that is transmitted through the region from the source while the C-shaped member is being driven along the axis of the support surface by the scanning motor;

rotating the C-shaped member, the x-ray radiation source and detector array about the support surface to a second angle with a motor such that the source and detector array are aligned through the region of interest at a second angle different from the first angle;

scanning the region of interest with the C-shaped member, x-ray source and detector array, the detector array receiving radiation from the source that is transmitted laterally through the region of interest to the detector array at the second angle while the C-shaped member is being driven along the axis of the support surface by the scanning motor;

determining bone density in the region of interest from radiation detected with the detector array at two energies transmitted through the region of interest during the scanning at least at one of the first angle and the second angle; and generating an image of the scanned region of interest on a display with radiation detected by the detector array.

17. The method of claim 16 further comprising providing a second motor to drive the C-shaped member in a second direction that is perpendicular to the first direction.

18. The method of claim 16 further comprising directing a fan beam of x-ray radiation through the patient during scanning and detecting said fan beam with said detector array.

19. The method of claim 16 further comprising displacing the C-shaped member to one side of the region of interest after scanning at the first angle and before rotating the C-shape member to the second angle.

20. The method of claim 16 further comprising directing laser light onto the patient to identify a position of the C-arm and recording the position of the C-shaped member relative to the support surface.

21. The method of claim 20 further comprising indicating on the display a position on the patient illuminated with the laser.

22. The method of claim 16 wherein the step of scanning at the first angle further comprises scanning at an oblique angle relative to the support surface.

23. The method of claim 16 further comprising determining a distance of a region within the scanned region of the patient.

24. The method of claim 16 further comprising providing relative movement between the support surface and the C-shaped member before rotating the C-shaped member to the second angle.

25. The method of claim 16 further comprising positioning the x-ray radiation source under the support surface during scanning at the first angle.

* * * * *